US009480641B2

(12) United States Patent
Perez Davidi et al.

(10) Patent No.: US 9,480,641 B2
(45) Date of Patent: Nov. 1, 2016

(54) METHODS AND COMPOSITIONS FOR TREATMENT OF HALITOSIS

(71) Applicants: Michael Moshe Perez Davidi, Savion (IL); Nir Sterer, Hod Hasharon (IL); Ervin Itzchak Weiss, Hertzlia (IL)

(72) Inventors: Michael Moshe Perez Davidi, Savion (IL); Nir Sterer, Hod Hasharon (IL); Ervin Itzchak Weiss, Hertzlia (IL)

( * ) Notice: Subject to any disclaimer, the term of this patent is extended or adjusted under 35 U.S.C. 154(b) by 0 days.

(21) Appl. No.: 14/589,717

(22) Filed: Jan. 5, 2015

(65) Prior Publication Data

US 2016/0000695 A1    Jan. 7, 2016

Related U.S. Application Data

(60) Continuation-in-part of application No. 13/163,706, filed on Jun. 19, 2011, now abandoned, which is a division of application No. 12/440,024, filed as application No. PCT/IL2007/001024 on Aug. 15, 2007, now abandoned.

(60) Provisional application No. 60/824,476, filed on Sep. 5, 2006.

(51) Int. Cl.
| A61K 9/00 | (2006.01) |
| A61K 8/97 | (2006.01) |
| A61K 8/02 | (2006.01) |
| A61Q 11/00 | (2006.01) |
| A61K 36/22 | (2006.01) |
| A61K 36/28 | (2006.01) |
| A61K 36/53 | (2006.01) |
| A61K 36/537 | (2006.01) |
| A61K 9/20 | (2006.01) |

(52) U.S. Cl.
CPC ............... *A61K 8/97* (2013.01); *A61K 8/0204* (2013.01); *A61K 8/0208* (2013.01); *A61K 9/006* (2013.01); *A61K 36/22* (2013.01); *A61K 36/28* (2013.01); *A61K 36/53* (2013.01); *A61K 36/537* (2013.01); *A61Q 11/00* (2013.01); *A61K 9/2054* (2013.01)

(58) Field of Classification Search
CPC ...................................... A61K 9/53
See application file for complete search history.

(56) References Cited

FOREIGN PATENT DOCUMENTS

JP          2005154339 A    *    6/2005

* cited by examiner

*Primary Examiner* — Benjamin Packard
(74) *Attorney, Agent, or Firm* — Mark David Torche; Patwrite LLC

(57) ABSTRACT

Methods and compositions for treatment of halitosis are provided; devices and methods, such as a palatal patch, including a tablet or strip having a bioadhesive component and active ingredients are further provided; the bioadhesive component allows for the palatal patch to be attached to the upper palate and for the active component to be released into the oral cavity and/or GI tract; compositions for the active ingredient include composition for treatment of halitosis, anti-acids, vitamins, anti-smoking agents, etc; an herbal composition for treatment of halitosis including *Echinacea*, Lavender, Mastic Gum and Sage and a method of manufacturing a medicine from the herbal composition are provided as well; a device for delivery of the palatal patch to the upper palate including a housing and piston is also provided.

18 Claims, 15 Drawing Sheets

METHODS AND COMPOSITIONS FOR TREATMENT OF HALITOSIS

CROSS REFERENCE TO RELATED APPLICATIONS

The present application is continuation-in-part application of and claims the benefit of domestic priority to U.S. patent application Ser. No. 13/163,706 filed Jun. 19, 2011 entitled "COMPOSITIONS FOR TREATMENT AND USE OF A PALATAL PATCH".

U.S. patent application Ser. No. 13/163,706 is a divisional application of and claims the benefit of domestic priority to U.S. patent application Ser. No. 12/440,024, filed Mar. 5, 2009, entitled "Systems, Methods, and Compositions for Treatment and Use of a Palatal Patch" that is a national stage entry of PCT/IL07/01024, which claims the benefit of priority from U.S. provisional application 60/824,476. The aforementioned applications are hereby incorporated by reference herein.

TECHNICAL FIELD

In general, the present invention pertains to the art of herbal pharmaceutical treatment. More specifically the present invention relates to an herbal composition including *Echinacea*, Lavender, Mastic Gum and Sage, which is useful for treatment of halitosis, as well as to method of manufacturing a medicine for the treatment of halitosis having as active ingredient the aforementioned herbal composition.

BACKGROUND OF THE INVENTION

Oral malodor (Halitosis, Fetor ex ora) is a common and disturbing condition, affecting according to some studies about one quarter of the population. This condition may start at any time from early childhood through adolescence, adulthood and old age and may vary in character and severity. Research has pointed to bacterial putrefactive activity as the primary cause of this condition. The bacteria responsible for malodor production are for the most part Gram negative oral bacteria such as Porphyromonas *gingivalis, Fusobacterium nucleatum* and *Prevotella intermedia*. These bacteria reside on various locations within the oral cavity (e.g. tongue dorsum, inter-dental space, periodontal pockets, tonsils) and break down salivary and oral proteins into their amino acid building blocks. Some of these amino acids (e.g. methionine, cysteine, tryptophan, lysine) are further metabolized, yielding malodorous volatile products such as methylmercaptan, hydrogen sulfide, indole, skatole and cadaverine. These are foul smelling compounds, which are released during exhalation and speech.

The oral environment is used as a point of entry for drugs and medications. Frequently the medicament passes quickly through the oral cavity to be absorbed in the gastrointestinal tract. In some of the cases it would be advantageous for the medicament to stay in the oral cavity for a prolonged period of time and to release the active ingredients in a sustained and controlled manner to be swallowed and absorbed in the gastrointestinal system (GIS). It is common knowledge that the pH of the gastrointestinal tract and the oral cavity differ and is a factor affecting the medicaments chemically and physically. It is in some cases desired to keep the medicament in the mild conditions of the oral cavity.

It is therefore an object of the present invention to provide compositions for treating malodor, and devices for delivery of such compositions as well as other potential medicaments to the oral cavity and gastrointestinal tract.

SUMMARY OF THE INVENTION

The oral environment is used as a point of entry for drugs and medications. Frequently the medicament passes quickly through the oral cavity to be absorbed in the gastrointestinal tract. In some of the cases it would be advantageous for the medicament to stay in the oral cavity for a prolonged period of time and to release the active ingredients in a sustained and controlled manner to be swallowed and absorbed in the gastrointestinal system (GIS). It is common knowledge that the pH of the gastrointestinal tract and the oral cavity differ and is a factor affecting the medicaments chemically and physically. It is in some cases desired to keep the medicament in the mild conditions of the oral cavity. It is therefore an object of the present invention to provide compositions for treating malodor, and devices for delivery of such compositions as well as other potential medicaments to the oral cavity and gastrointestinal tract.

An upper surface having a curvature defined by a top segment, a bottom segment, and a slanted segment connecting the top segment to the bottom segment, the curvature configured to approximate a shape of an upper palate, a lower surface connected to the upper surface at the bottom segment of the upper surface, a bioadhesive component incorporated into the device, and an active component incorporated into the device.

According to further embodiments of the present invention, there is provided a method for providing an active ingredient to a GI tract. The method includes providing a device having a bioadhesive component and an active component, adhering the device to an upper palate via the bioadhesive component, and releasing the active component into the oral cavity and GI tract.

According to further embodiments of the present invention, there is provided a composition for treatment of halitosis. The composition includes at least two of: *Echinacea*, Lavender, Mastic Gum and Sage.

According to further embodiments of the present invention, there is provided a device for delivery of a palatal patch to an upper palate. The device includes a housing having a distal end and a proximal end, a piston positioned within the housing, the piston including a piston stem, a piston controller at a proximal end of the piston stem, and a holder at a distal end of the piston stem, the holder configured to hold a palatal patch therein, and a spring having a spring distal end and a spring proximal end, the spring distal end attached to the piston in a vicinity of the holder, the spring proximal end attached to the housing, wherein the piston controller is configured to push the piston stem and holder distally, and wherein upon release of the piston controller, the spring is configured to return the piston stem and holder to a proximal position.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The present invention will be understood and appreciated more comprehensively from the following detailed description taken in conjunction with the appended drawings in which.

Figure 1A:
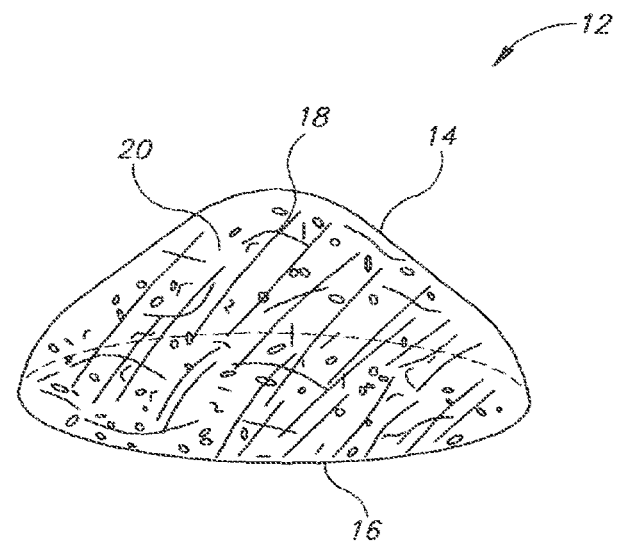
FIGS. 1A and 1B are perspective and cross-sectional illustrations of a device for oral bioadhesion, in accordance with embodiments of the present invention.

While the invention is susceptible to various modifications and alternative forms, specific embodiments thereof have been shown merely by way of example in the drawings. The drawings are not necessarily complete; emphasis is instead being placed upon clearly illustrating the principles underlying the present invention.

DETAILED DESCRIPTION OF THE INVENTION

Illustrative embodiments of the invention are described below. In the interest of clarity, not all features of actual implementation are described in this specification. It will of course be appreciated that in the development of any such actual embodiment, numerous implementation—specific decisions must be made to achieve the developers' specific goals, such as compliance with technology—or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to systems and methods for oral-based treatments. The principles and operation of a system and methods according to the present invention may be better understood with reference to the drawings and accompanying descriptions.

Figure 1B:
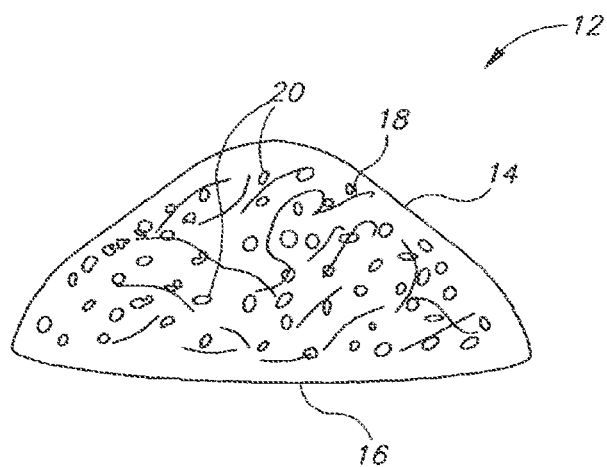

Reference is now made to FIG. 1A, which is an illustration of a device 12 for oral bioadhesion. In the embodiment shown in FIGS. 1-6, device 12 is a tablet device, which is configured to the approximate shape of an upper palate. Device 12 includes an upper surface 14 and a lower surface 16, wherein upper surface 14 is curved to approximate the shape of the upper palate, lower surface 16 is connected to upper surface 14 and upper surface 14 and lower surface 16 define a surface area. In the embodiment shown herein, lower surface 16 is substantially flat, although lower surface 16 may also be curved similar to upper surface 14. Lower surface 16 may be circular, oval, or any other configuration without sharp edges so as not to damage the oral cavity or cause discomfort to the user. In this embodiment, device 12 is a solid tablet and is comprised of a bioadhesive component 18 and an active component 20. Bioadhesive component 18 includes adhesive materials for temporarily adhering device 12 to the upper palate. Active component 20 includes a substance or composition which can be released into the oral cavity and its tissues and used to treat the oral cavity and/or the GI tract and deliver active agents in a continuous pattern to the GI system. In other embodiments, device 12 may be a strip which is flexible enough to adhere to and conform to a shape of an upper palate. A cross-sectional illustration of device 12 in a tablet configuration is shown in FIG. 1A. In the embodiments shown in FIGS. 1A and 1B, bioadhesive component 18 and active component 20 are mixed together preferably in a way in which a homogenous mixture of both the bioadhesive and active ingredients can be achieved.

Device 12 may be formed into a tablet by combining bioadhesive component 18 and active component 20, and by pressing the composition into a press such as Carver laboratory press (Carver Machine Works, Inc., IN, USA). Tablets may have varying dimensions, but should be appropriate for an upper palate, without protruding too much in any direction so as not to cause discomfort. For example, an appropriate sized tablet for a human adult may be in a range of 5-15 mm in diameter and 0.1-4 mm thickness. An appropriate sized tablet for a child may in a range of 2-8 mm in diameter, and for an animal such as a dog, may be in a range of 2-15 mm in diameter. It should be readily apparent that the sizes may vary, and should be determined according to the average sizes of upper palates in each category of users.

Figure 2:
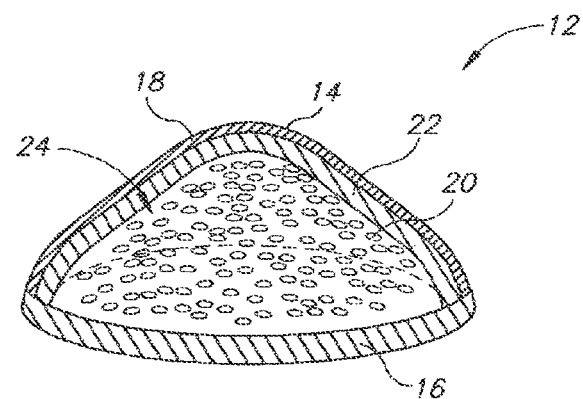
FIG. 2 is a cross-sectional illustration of a device for oral bioadhesion in accordance with additional embodiments of the present invention, wherein the device further includes a release-controlling substance.

Reference is now made to FIG. 2, which is a cross-sectional illustration of device 12 in accordance with another embodiment of the present invention. In this embodiment, device 12 further includes a release-controlling substance 22, which is configured to degrade and slowly release active component 20 over time. Release-controlling substance 22 forms a compartment 24 which can hold active component 20 therein. Release-controlling substance 22 may be any biodegradable material such as a biodegradable polymer, and the properties of release-controlling substance 22 may be adjusted to control the degradation time and thus the release time of active component 20. As shown in FIG. 2, bioadhesive component 18 is positioned outside of compartment 24 and preferably in a vicinity of upper surface 14. In some embodiments, bioadhesive component 18 forms upper surface 14.

Figure 3:
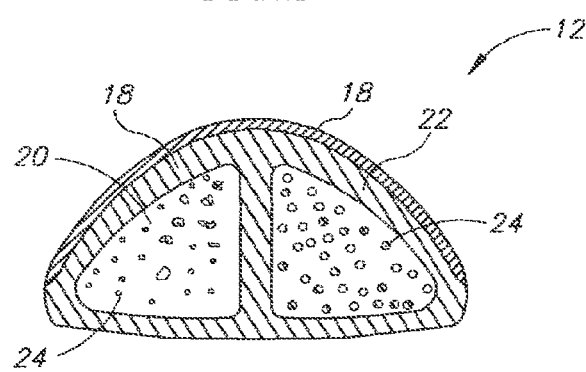
FIG. 3 is a cross-sectional illustration of a device for oral bioadhesion in accordance with additional embodiments of the present invention, wherein multiple compartments are present.

Reference is now made to FIG. 3, which is a cross-sectional illustration of device 12 in accordance with additional embodiments of the present invention. As depicted in FIG. 3, multiple compartments 24 are present, wherein each of multiple compartments 24 may have different characteristics, such as different active components 20 and/or different release-controlling substances 22. In this way, different active components 20 may be released at different rates, providing, for example, immediate or acute treatment as well as long-lasting treatment. The rate of release of active component 20 will depend on the material properties of release-controlling substance 22, and may be designed to fit particular treatment plans.

Figure 4:
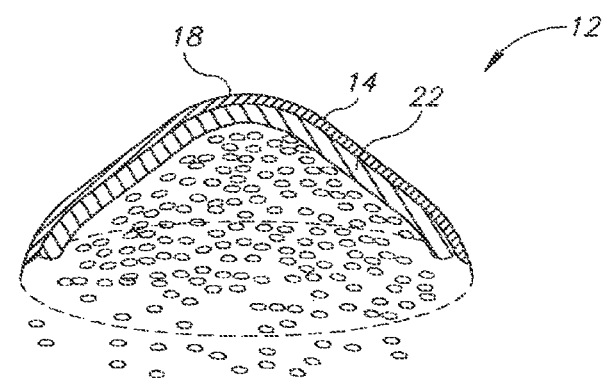
FIG. 4 is a cross-sectional illustration of the device of FIGS. 2 and 3, depicted as degradation of release-controlling substance 22 has begun and showing the release of an active component from within the device.

Reference is now made to FIG. 4, which is a cross-sectional illustration of device 12 as degradation of release-controlling substance 22 has begun showing the release of active component 20 from within device 12. It should be apparent that in the embodiments wherein release-controlling substances 22 are not used, active component 20 will still be released out of device, either by dissolving into the oral cavity or by degradation of bioadhesive component 18, which may be comprised of biodegradable material as well.

Figure 5:
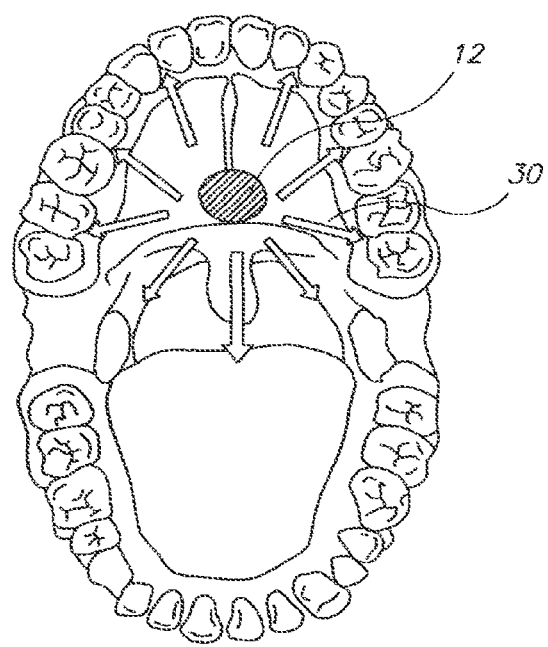
FIG. 5 is a schematic illustration of an upper palate with a device for oral bioadhesion in place on the upper palate.
Figure 6:
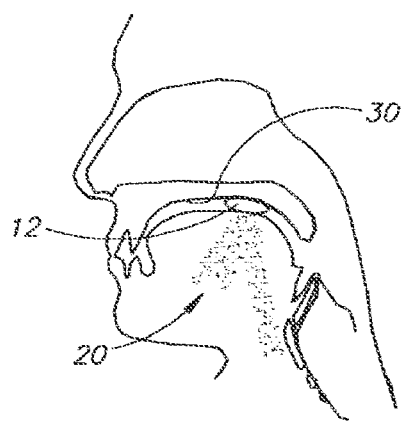
FIG. 6 is a schematic illustration of the device on the upper palate, showing the active component being released into the oral cavity and into the esophagus and GI tract.

Reference is now made to FIG. 5, which is a schematic illustration of an upper palate 30 with device 12 in place. Generally device 12 is placed on the highest portion of upper palate 30, although any location on upper palate 30 may be used. Device 12 is positioned in place and held for an amount of time sufficient to cause bioadhesive component 20 to adhere to upper palate 30, which will depend on the amount and composition of bioadhesive component 20. Reference is made to FIG. 6, which is a schematic illustration of a side view of upper palate 30, with device 12 in place. Active component 20 is also depicted as it is released from device 12. Release of active component 20 continues until device 12 is completely dissolved. As shown in FIG. 6, because of its location on upper palate 30, active component 20 is configured to be released into the oral cavity and into the esophagus and GI tract, thus providing a wide range of potential treatments. In some embodiments, release of active component 20 may be controlled by the tongue of the user.

Figure 7:
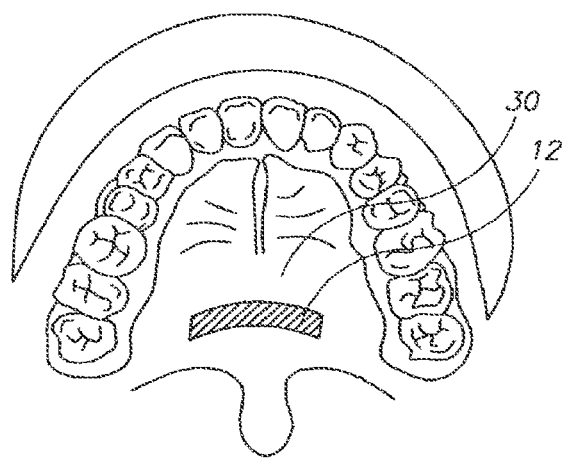
FIG. 7 is a schematic illustration of the upper palate with a device for oral bioadhesion in place, wherein the device is a strip or patch.

Reference is now made to FIG. 7, which is a schematic illustration of upper palate 30 with device 12 in place, wherein device 12 is a strip or patch. In this embodiment, device 12 may be relatively flexible and thus may conform to the shape of upper palate 30 upon placement thereon. One way of preparing a strip is by casting a concentrated suspension in ethanol of all ingredients onto a flat surface which after solvent evaporation, a thin sheet is obtained. The sheet is then cut into the desired size and shape using a cutting mold. The concentrated suspension can be molded into a mold of the desired shape which results in the device formation after solvent evaporation.

Bioadhesive component 18 may be comprised of a polymeric material including natural polymers, semisynthetic polyhydric polymers, synthetic polyhydric polymers or polycarboxylic acid polymers, hydrocolloids, or combinations thereof. (Examples of polyhydric polymers which can be used as bioadhesive component 18 include hydroxypropyl cellulose, hydroxypropyl methylcellulose, hydroxyethylcellulose, carboxymethyl cellulose, dextran, arabinogalactan, pullulan, gaur-gum, hyaluronic acid, pectins, starch derivatives, acrylic acid polymers, polymers of acrylic acid esters acrylic acid copolymers, polymers of vinyl alcohols, alkoxy polymers, chitosan, polyethylene oxide polymers, and polyethers or combinations thereof.

Suitable adhesive carriers include any of the non-toxic polymers, particularly those of the type used to carry drugs, including carboxylic acid containing polymers such as copolymers of acrylic or methacrylic acid, copolymers of maleic acid, and polysaccharides such as karaya gum, tragacanth gum, pectin, guar gum, alginates, hydrocolloid gels prepared from polysaccharides extracted from Fronia elephantum, Sapindus trifoliatus, Kunjac, cashew tree, cellulose and cellulose derivatives such as methyl cellulose, propyl cellulose, cellulose acetate and the like, along with other substances known for use in transdermal preparations capable of forming a solid colloid that can adhere to tissue, used alone or in combination with other suitable carriers. One preferred carrier is a bioadhesive for application to the mucosa composed of mixtures of slightly crosslinked polyacrylic acid, i.e. Carbopol 940, 934, 970, 974, and the like, carboxymethyl cellulose and hydroxypropylmethyl cellulose (HPMC).

The term "adhesive" as used herein means a substance, inorganic or organic, natural or synthetic, that is capable of surface attachment to the intended oral cavity application site. The term "bioadhesive" as used herein means an adhesive which attaches to mucosal tissue upon hydration. It is preferred that the attachment be a relatively strong attachment. To qualify as a bioadhesive, a substance must be capable of maintaining adhesion in moist or wet in vivo environments. The devices of the present invention are also self-adhesive in that they attach to the site of interest without the need for reinforcement by way of another adhesive which is applied to a backing.

The strength of adherence can be measured by standard tests for measuring force, e.g. in dynes per square centimeter, as disclosed in U.S. Pat. No. 4,615,697. Suitable bioadhesives include those prepared from optionally partially esterified polyacrylic acid polymers, including but not limited to, polyacrylic add polymers lightly crosslinked with a polyalkenyl polyether such as those commercially available from B.F. Goodrich, Cincinnati, Ohio, under the trademarks Carbopol 934, 934P, 974, 940 and 941.

Other suitable bioadhesives include natural or synthetic polysaccharides. Suitable polysaccharides include cellulose derivatives such as, cellulose acetate, carboxymethylcellulose, hydroxyethylcellulose and the like. Other suitable bioadhesives are pectin, a mixture of sulfated sucrose and aluminum hydroxide, hydrophilic polysaccharide gums such as natural plant exudates, including karaya gum, ghatti gum, tragacanth gum, xanthan gum, jaraya gum and the like, as well as seed gums such as guar gum, locust bean gum, psyllium seed gum and the like. The term non-finite carrier refers to any liquid or semi liquid known for or suitable for use in pharmaceutical preparations as will be apparent to one skilled in the art.

In addition to the above ingredients, there may also be incorporated other additives selected from among the various pharmaceutically acceptable additives available to those skilled in the art. These additives include fillers, tableting excipients, lubricants, enhancers, pH controlling compounds, dyes, binders, enzyme inhibitors, stabilizers, preservatives, flavorings and pigments. In a preferred finite form embodiment, the compositions of the present invention also contain a binder such as lecithin which "binds" the other ingredients, thereby enhancing the uniform consistency of the final composition. The active agent is loaded into the composition in as high a concentration as necessary to affect therapy.

Active component 20 is in one embodiment an herbal treatment for preventing halitosis. Herbal substances which have been shown by the present inventors to reduce halitosis effects, alone and in combination, include *Echinacea*, Lavender, Mastic Gum and Sage and further may include Propolis. A study showing the efficacy of such substances in reducing halitosis is presented hereinbelow in the Examples section.

In other embodiments, active component 20 may include antibiotics, anti-acids, expectorant (such as ROBITUSSIN), morphine, vitamins and smoking cessation products or combinations thereof. It should be readily apparent that active component 20 may be any medication, treatment or substance that can be released into the oral cavity and/or the GI tract.

Some examples of device 12 as created into a tablet form are as follows. These examples are illustrative and should not be regarded as limiting. Hydroxypropylcellulose (HPC) and Carbopol (CP) 940 are mixed with the active ingredient. The active ingredient is, for example, an herbal formulation. In one embodiment, tablets are fabricated from two layers: an adhesive layer composed of muco-adhesive polymers (Polyacrylic acid (PAA) and Hydroxypropyl cellulose (HPC)) and an active ingredient layer composed of the tested active, formula excipients and from flavors. All ingredients may be gently mixed using a mortar and pestle. Adhesive layer powder mixture is inserted into a mold, followed by the second layer mixture powder, and compressed by a laboratory Carver press (Carver Machine Works, Inc., Washington, N.C.), using a pressure of 5 ton/cm 2 for 30 seconds. One example of ingredients is as follows:

An adhesive layer is comprised of 30-40 mg PAA and 10-15 mg HPC. Approximately 20-50 mg of total herbal ingredients are added. In addition, 10-15 mg of polyvinyl pyrrolidoen (PVP) K30 and 40-50 mg of PVP K90 are added as water soluble fillers. 80-140 mg of Xylitol (for sugar-free sweetening and filler) and 1-3 mg of flavor may be added as well. One method for preparing the tablets is by compression tablets using a press machine, single or multi punch. The powder of the final formulation is loaded in the punch of different diameters ranging from 5 to 15 mm and thickness of about 0.5 mm to 2.5 mm. The thickness is controlled by the amount of powder added, usually 100 mg to about 300 mg.

Because of the limited size of the device to be applied and the loading, the active agent should be concentrated to include as much as active agent as possible. In addition, because the device is prepared by molding of a powder mixture in a tableting machine, in some embodiments the composition should be in a free flowing powder form suitable for use with commercial tableting devices. Thus the active herbal agents are condensed into a concentrated powder. Usually, hydroalcoholic herb extracts, when dried from the solvents, form a sticky mass that cannot be incorporated homogeneously as flowing powder with the inert ingredients. Also, if essential oils are used as active agents they should be converted into powder.

To overcome this limitation, a method has been developed for the present invention wherein the active agents are absorbed into an inert free flowing powder at a high concentration, and are then mixed with the bioadhesive ingredients to a free flowing powder prior to press molding. Typically, a water soluble pharmaceutically acceptable component such as a sugar is added to the herb extract solution, and is then freeze-dried to obtain a powder. The amount of loading is given in terms of the amount equivalent to the dry weight in grams of the extracted plant per gram of inert absorbent material (sugar). For example, 2 g mannitol is dissolved into a given tincture of 100 ml prepared from the extraction of 10 g of plant and lyophilized to dryness to form a powder which weighs 2.5 grams. Each gram of this powder is equivalent to 4 grams of plant extract.

When essential oil is to be incorporated, the oil is absorbed in a suitable powdery absorbent. Typical absorbents include for example, kaoline, Kapectin, alumina, silica, polystyrene beads, polyacrylate beads, clay, microcrystalline cellulose, and other orally acceptable powders with oil absorption capacity. The use of a crude herbal material that is part of the bioactive agents in a powder form is used for oil absorption.

A method of preparing crude herbal material for extraction may be as follows:

1. Crude dry herbal materials are milled into fine powders using a proper milling device. Any grinding operation that achieves the respective particle size for extraction is acceptable. A purpose of the milling step is to have a consistently-sized crude herb powder. Crude herb extractability is a critical function of exposed surface area of crude herb powder to hydroalcohol mass ratio. To eliminate crude herb particle size as a process variable and since the various herbs have different water-holding capability (porosity/absorptivity), a singular particle size is preferred for process control. Depending on the specific type of crude herbs, milling produces a mix of coarse and fine dust particulates.

2. All milled crude herb powders are mixed in a blender to provide uniform particle size of crude herbs prior to extraction. Particle size of milled crude herbal powder is consistent following this step.

3. Crude Herbal Material Extractions in hydroalcoholic solution (either option is suitable) a.) Soxhlet option: About 1-60 parts of milled crude herbal powder are added to 100-5000 parts (process and/or deionized or equivalent grade) water: alcohol in a Soxhlet Extractor and then decanted. A Soxhlet extractor is one or more station continuous reflux extractor with internal condenser slowly feeding 4 to 100 degrees Celsius solution across the herb for up to 48 hours. b.) Ultrasonic option: Suitable alternate extraction processes for developing this water soluble extract include use of ultrasonic water extraction systems which can provide equivalent quality, depending on the herb, with up to 94% faster process cycles, hydrolysis extracting reactors, fixed bed extracting reactors, desorption extraction columns, and countercurrent extractors. Due to most commercial extraction process limitations, it is normal to have a small amount of particulates in this extract.

4. Water-extracted herbal liquid is filtered (e.g., 5 to 10 microns filter cartridge, fine screen or cheesecloth) or centrifuged to remove coarse and/or insoluble particulates.

5. Filtered water-extracted herbal liquid is concentrated, depending on herbal ingredient, up to a 50% soluble solids level. In addition to concentration by evaporation, alternate suitable process to achieve higher concentrations prior to final drying include freeze concentration, partial freeze drying, membrane separation, vacuum distillation and vacuum drying.

6. Concentrated herbal extract liquids are dried via commercial drying processes. Suitable dryers that are used include fluidized bed, vacuum plate, spray, drum-type and flash dryers. Drying efficiency is controlled for water content (<10%) and free water considerations to achieve shelf-stability. Yield of soluble powder from the drying process is used as key to optimize herb: water mass formula for extraction.

7. Dried pure solid herbal extract powders are sized and packaged for shipment. A desiccating material such as a silica gel or other suitable FDA-approved, drying agent can be used to control relative humidity and to improve shelf-life.

8. Dried pure solid herbal extract powder is now ready for reconstitution into oral care products.

Coatings can be applied to tablets as well. Typical hydrophobic powders suitable for this coating include: fatty acids and salts such as Mg- or Ca-stearate, triglycerides and fatty acid esters, ethyl cellulose, methyl methacrylate-methacrylic acid copolymers (Eudragit), and other pharmaceutically acceptable hydrophobic components. To improve the adherence between the coating and the tablet, the hydrophobic components are mixed with the carrier components, i.e. HPMC and Carbopol at a ratio of 30 to 70% by weight. Alternatively, single layer tablets may be prepared and the coating on one side applied by spray coating with an alcoholic solution or fine dispersion of the hydrophobic coating. The spray coating of one side can be applied on the automated machine where the tablets are placed onto a running sheet which is exposed to spray nozzles to spray coat the tablets. If a solvent cast method of preparation is used, the coating can be applied as a spray on top of the sheet loaded with the active agents. Other industrial methods can be applied including forming the sheet on an edible hydrophobic sheet such as rise paper and cut to devices.

In one embodiment, 15 mg of white powder composed on 50% Mg-stearate, 33% Carbopol 934, and 17% HPMC, is added to laboratory punch and slightly rotated to obtain a uniform surface. On top of this, 70 mg of a mixture composed of 7 mg of plant extract and 63 mg of a powder mixture of Carbopol 934, HPMC (2:1 weight ratio). The powder is compressed into a tablet at a pressure of 7 tons per sq. cm for 30 seconds. A uniform strong dark tablet with a white coating on one side is obtained.

An example of a multi-layer sticker is prepared by compression of three different powders, the first layer is a thin layer of self-adhesive powder, Carbopol 934: HPMC 2:1 w/w ratio loaded with benzocaine local anesthetic for initial pain relief, the second layer is loaded with the herbal active agents and the third layer is a capping layer of a hydrophobic and less water soluble layer. The main advantage of using a multilayer tablet is that each layer may contain different active agents that are exposed at a different time and rate to the mucosal surface for better treatment.

Components that may be used for inert self-bioadhesive polymer include: mixture of carboxymethyl cellulose, polyacrylic acid, and crosslinked arabinogalactan and dextran and polyethylene glycol that form a complex with the carboxylic acid residues of acrylates.

Figure 8:
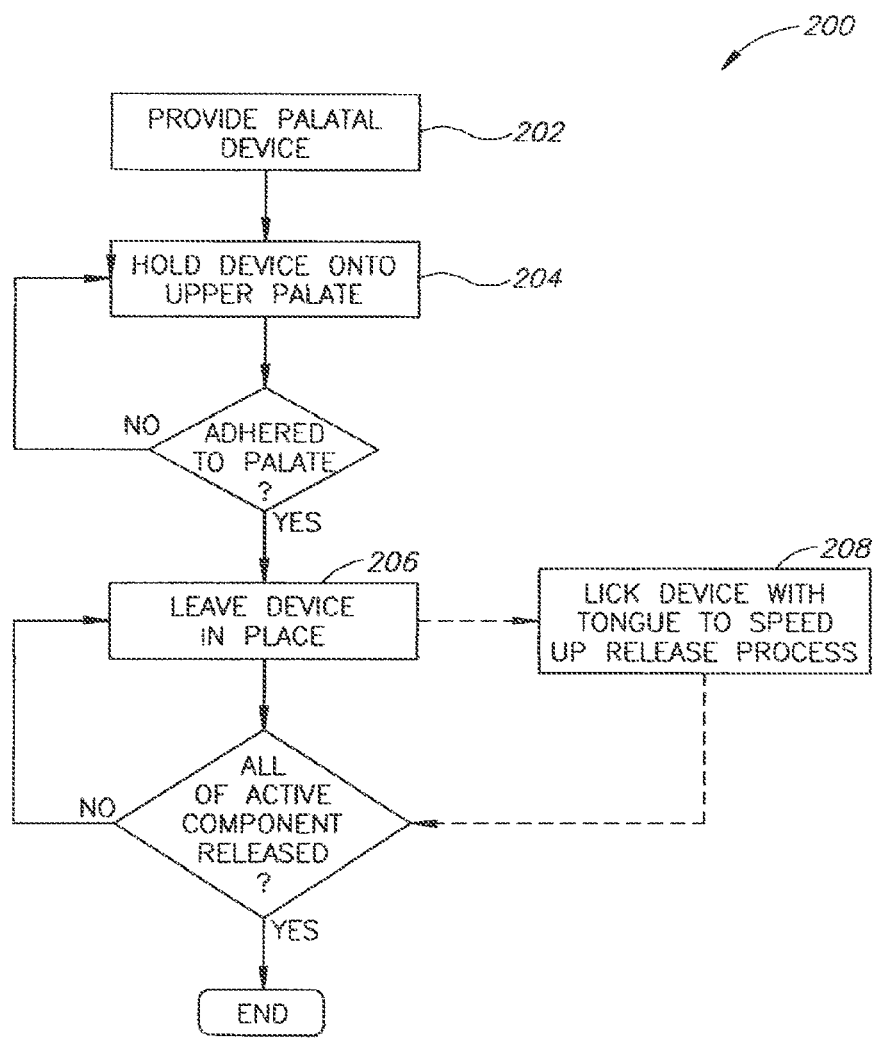
FIG. 8 is a flow-chart illustration of a method of providing treatment using devices of the present invention.

Reference is now made to FIG. 8, which is a flow-chart illustration of a method 200 of providing treatment. First, a device 12 including a bioadhesive component 18 and an active component 20 is provided (step 202). Device 12 is placed on an upper palate, and held in place (step 204) for a period of time sufficient to allow for bioadhesive component 18 to adhere to the upper palate. This period of time depends on the material properties and concentrations of bioadhesive component 18. In one embodiment, the period of time is approximately 5 seconds. This can be accomplished, for example, by providing adhesive layers that are mixtures of Carbopol and Hydroxpropyl cellulose at approximately 1:1 w/w to 100% Carbopol-crosslinked polymethacrylic acid. Increase in Carbopol increases adhesion forces and adhesion time. In certain circumstances, it may be beneficial to change the amount of time. For example, when using device 12 with an animal, such as a dog, the period of time may be reduced to 1 second or less. This can be accomplished, for example, by elevating the concentration range of Carbopol to 180-220 mg and by using Carbopol 940. After the period of time, device 12 is left in place (step 206), while active component 20 is released into the oral cavity and the GI tract. This action continues until device 12 is completely dissolved. The time to dissolution may vary from less than an hour, to several days, and portions of device 12 may dissolve at varying rates. Optionally, the rate of dissolution may be increased by periodically licking (step 208) device 12 with the tongue. In some embodiments, the licking action can completely control the release of active component 20 such that active component 20 is only released by licking of the tongue.

Delivery System

Figure 9A:
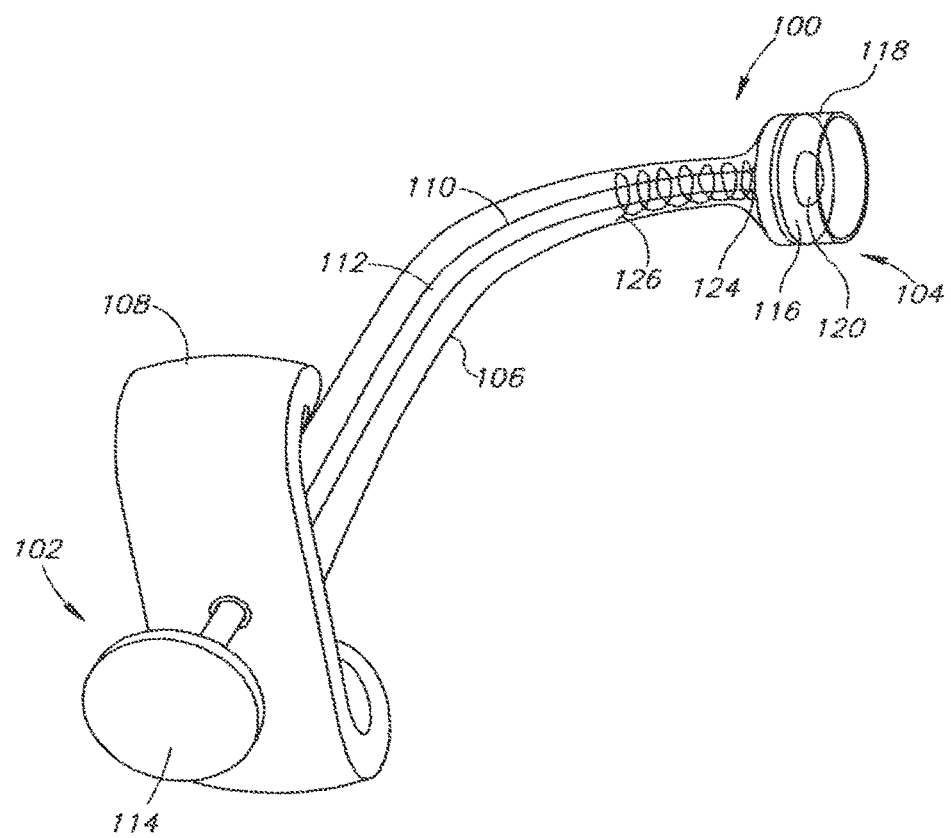
FIGS. 9A and 9B are illustrations of a delivery system for delivery of a device to an upper palate.
Figure 9B:
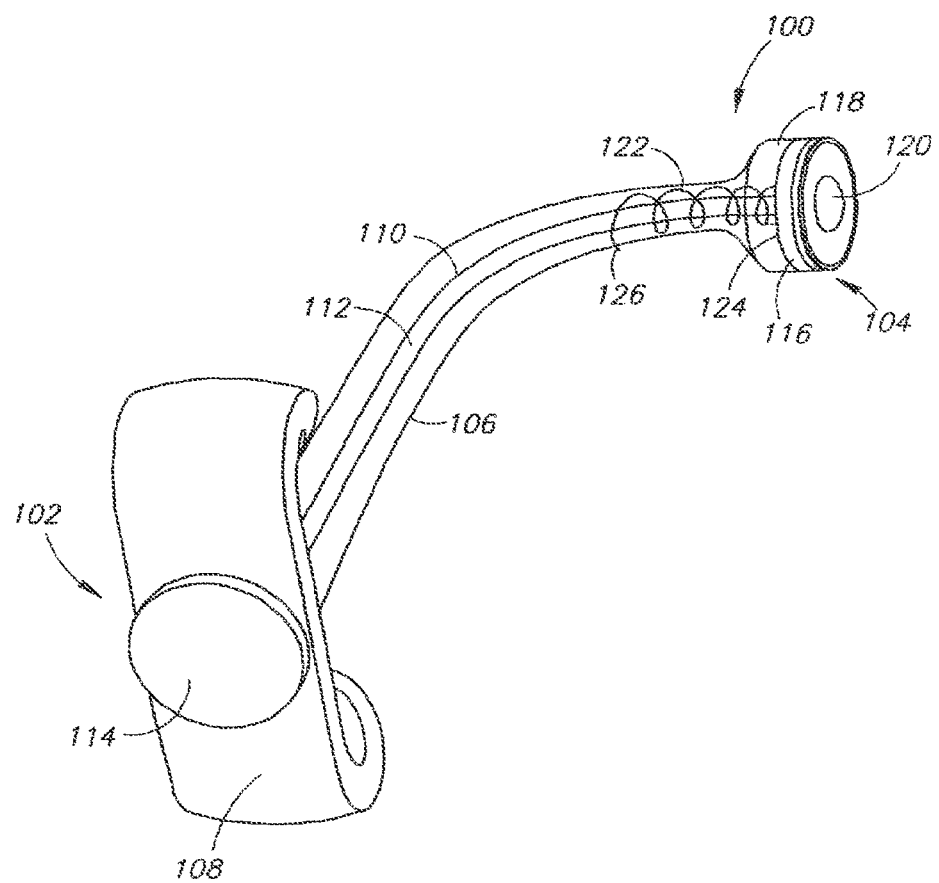

Reference is now made to FIGS. 9A and 9B, which are illustrations of a delivery system 100, for delivery of device 12 to an upper palate. Delivery system 100 may be particularly useful for placing device 12 on an upper palate of an animal such as a dog, where direct placement via a hand would be difficult or dangerous. Delivery system 100 has a proximal end 102 and a distal end 104, wherein distal end 104 is configured to enter the mouth. A housing 106 extends from proximal end 102 to distal end 104 and may be slightly curved, particularly in a vicinity of distal end 104. A handle 108 is positioned at proximal end 102 of housing 106 for holding delivery system 100. A piston 110 positioned within housing 106 includes a piston stem 112 extending along the length of housing 106 and internally with respect to housing 106, a piston controller 114 at proximal end 102, and a holder 116 at distal end 104. Holder 116 is configured to hold device 12 therein. Thus, for example, holder 116 may include a tablet depression 120 which is sized to fit device 12 when device 12 is in a tablet configuration. Alternatively, holder 116 may include prongs or some other mechanism to hold device 12 in place until it is delivered. Holder 116 is positioned within an outlet portion 118 at distal end 104 of housing 106. Piston 110, including piston stem 112, piston controller 114 and holder 116, may be pushed distally until holder 116 reaches distal end 104.

In some embodiments, holder 116 may be pushed past distal end 104. Distal pushing movements are initiated by pushing piston controller 114 distally. A distal end of a spring 122 is attached to piston 110 at a spring/piston attachment point 124, which is generally located at or on holder 116, and a proximal end of spring 122 is attached to housing 106 at a spring/housing attachment point 126. This allows for piston 110 to resume its original position after the user releases piston controller 114. As shown in FIG. 9A, piston 110 is by default in its more proximal position, wherein holder 116 and device 12 are positioned within outlet portion 118. As shown in FIG. 9B, when piston controller 114 is pushed distally, piston 110 moves into its distal position wherein holder 116 is at or distal to distal end 104, and device 12 can be delivered.

Formulation Methods

In further embodiments of the present invention, an herbal composition for treatment of halitosis is provided. The herbal composition includes at least one of the following ingredients: *Echinacea* (*Echinacea augustifblia*) root, Mastic gum (*Pestacia lentiscus*) resin, Lavender (*lavandula augustifolia*) flowers and Sage (*salvia officinalis*) leaves. In a study presented hereinbelow, these herbs, alone and in combination, were shown to have a significant effect on malodor.

As described herein, groups of herbs can be chosen and combined according to their biological activities. Each herbal component selected in this group is known, but their combination, or sub-combinations, is a new concept. Moreover, these herbs and more particularly combinations thereof have not previously been identified for reduction of malodor or halitosis. When combined according to the teachings described herein, a composition provides synergistic benefits/results toward the treatment of halitosis. Certain embodiments use a plurality of herbs and/or herbal extracts to manufacture an herbal composition. One embodiment provides a composition of approximately four herbs and their extracts which, based on studies, described herein, are useful for the treatment or improvement of halitosis or malodor.

In some embodiments, components may be provided in dried or lyophilized form. Alternative embodiments may use macerated, ground, chopped, cooked, extracted, and other forms of the herb as components of embodied compositions. The compositions may be provided in various formats, such as a tablet, patch, toothpaste, candy, mouthwash, chewing gum, or others. A mouthwash solution can be prepared by lyophilizing the herbal formula and dissolving the extract in water. In one embodiment, the concentration of the active ingredients would be in the range of 30-60 mg/100 ml. Other components of the solution can include flavor (0.1-3 mg) sweeteners (50-150 mg) and ethanol (0-0.4%). Similarly, toothpastes may be made by lyophilizing the herbal formula and dissolving the extract in a toothpaste base, a chewing gum base or a candy base. The extract can then be dissolved or dispersed in water or alcohol or mixtures thereof, and then reconstituted with other active ingredients such as: sodium fluoride 0.32%, triclosan 0.3% and other ingredients such as glycerin, Aqua, Hydrated silica, PVMMA Copolymer, aroma, sodium lauryl sulfate, cellulose gum, Canrageenan, sodium hydroxide, sodium fluoride, triclosan, sodium saccharin, limonene, ci42090, ci47005 and others.

Combinations of the ingredients described can improve the overall benefit and/or effect of each of the ingredients individually. In one embodiment, extracts of *Echinacea* root, Mastic gum resin, Lavender flowers and Sage leaves may be mixed in a 1:1:1:1 ratio and made into tablet. In another embodiment, the components may be mixed in other ratios.

The herbal composition of the invention is typically formulated with a suitable pharmaceutical excipient, having a predefined dissolution rate within the saliva secreted into oral cavity. The dissolution rate of the pharmaceutical excipient is optionally defined by Equation 1, as well as any known equation, such as the Noyes-Whitney or the Nernst and Brunner equation, wherein: m is the mass of dissolved material and t is time variables to be determined; whereas the other values are inherent properties of the formulation, namely: A is the surface area of the interface between the dissolving substance and the solvent; D is diffusion coefficient, d is thickness of the boundary layer of the solvent at the surface of the dissolving substance, $C_s$ is the mass concentration of the substance on the surface and $C_b$ is the mass concentration of the substance in the bulk of the solvent.

$$\frac{dm}{dt} = A\frac{D}{d}(C_s - C_b) \qquad \text{Equation 1}$$

Figure 19:
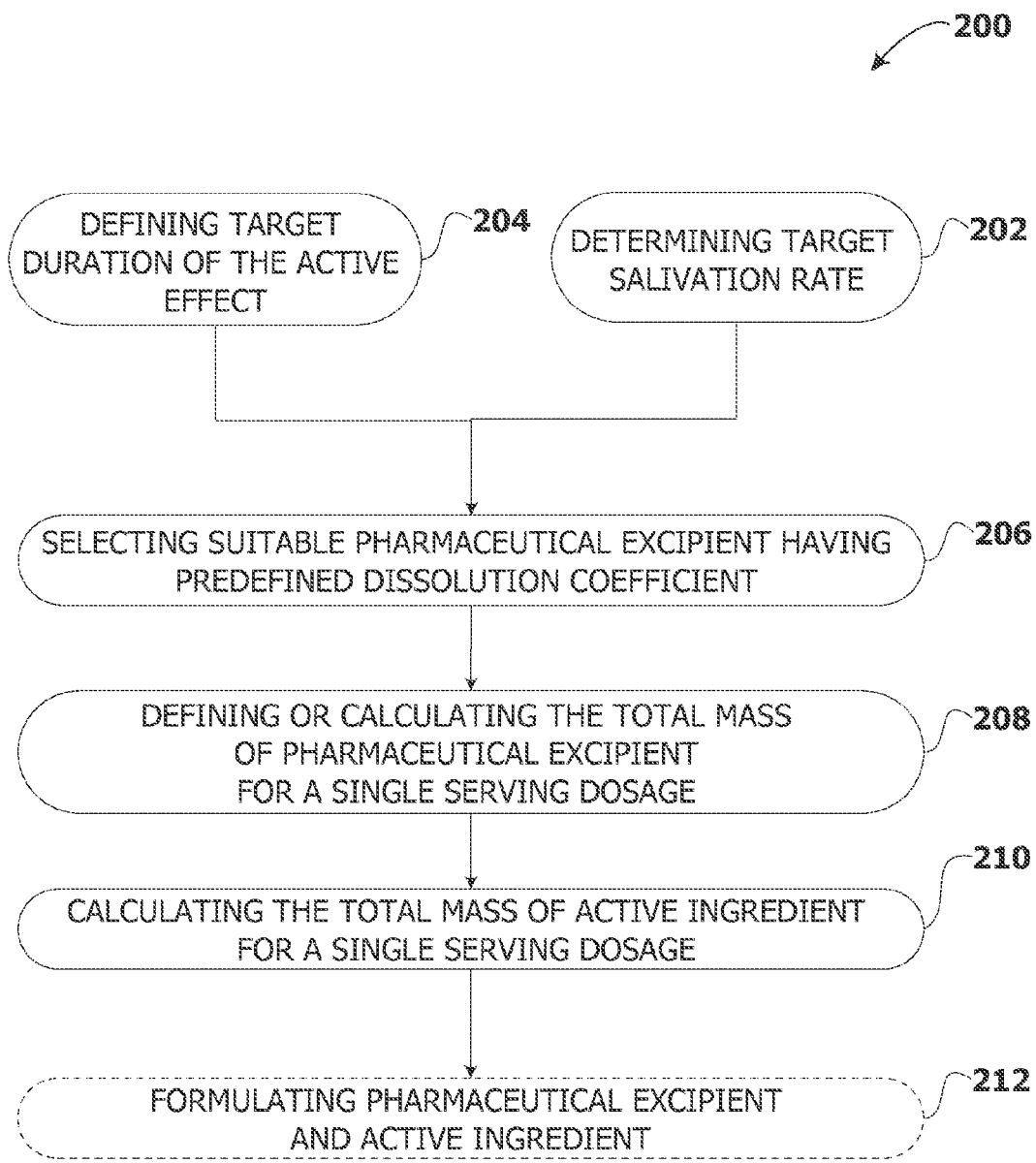
FIG. 19 is a flowchart showing a method of manufacturing a medicine with an active ingredient of the herbal composition of the invention.

Reference is now made to FIG. 19, showing the flowchart of method 200 of manufacturing a medicine with an active ingredient of the herbal composition of the invention. Initially a target salivation rate is determined, at step 202. For instance an average unstimulated saliva flow rate of 0.3-0.4 ml per minute can be assumed for a normal grown individual. Then the target duration for the medicine is defined at step 204 and taken as the dt value in the above noted Equation 1. Thereafter, a suitable pharmaceutical excipient is selected, at step 206, having a predefined diffusion coefficient D and the rest of the values of Equation 1 are completed based of serving form of the formulated medicine, which differs between a sublingual tablet, to a supralingual tablet and palatal patch.

The dm is consequently calculated at step 208 and preferably taken as 70% to 80% of the total mass of the pharmaceutical excipient to be used for a single serving dosage. Alternatively the target duration for the medicine is defined at step 204 and taken as the dt value in Equation 1 and the total mass of the pharmaceutical excipient to be used for a single serving dosage is also predefined at step 208 and taken as the value dm in the above noted Equation 1, whereas the desired diffusion coefficient D is then calculated and the appropriate pharmaceutical excipient is selected at step 206 based on the calculated diffusion coefficient D.

The amount of active ingredient is then calculated, at step 210, based on the ratio to the total mass of the pharmaceutical excipient, so that during the target duration for the medicine defined at step 204 the amount of the active ingredient released upon dissolution of the pharmaceutical excipient essentially does not exceed one percent of weight of each one of the herbal components of the herbal composition, namely *Echinacea*, Lavender, Mastic Gum and Sage, per volume of said saliva, secreted at the aforementioned salivation rate, determined at step 202. The calculated amounts of the pharmaceutical excipient and active ingredient are ultimately formulated together, at step 212, optionally with other formulation substances.

WORKING EXAMPLES

The following examples are included to demonstrate the working effect of preferred embodiments. It should be appreciated by those of skill in the art that the techniques disclosed in the examples which follow represent techniques discovered to function well, and thus can be considered to constitute preferred modes for its practice. However, those of skill in the art should, in light of the disclosure, appreciate that many changes can be made in the specific embodiments which are disclosed and still obtain a like or similar result without departing from the spirit and scope of the embodiments.

While compositions and methods have been described in terms of preferred embodiments, it will be apparent to those of skill in the art that variations may be applied to the compositions and methods described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

Example 1

Materials and Methods

In vitro study: A salivary incubation assay was used to examine the effect of the natural medicinals (*Echinacea* (*Echinacea augustifolia*) root, Mastic gum (*Pestacia lentiscus*) resin, Lavender (*lavandula a*[upsilon]g[upsilon]*stifolia*) flowers and Sage (*salvia officinals*) leaves) and their combination on malodor production and malodor related parameters. These parameters included: (i) a quantified measurement of headspace volatile sulfide compounds (VSC), (ii) salivary protein analysis in order to determine protein degradation, (iii) microbial counts and microscopic evaluation to determine selective and general antimicrobial ability of each medicinal and (iv) pH. These parameters are important in assessing the effectiveness of each substance in reducing malodor as well as understanding its mechanism of action.

Filtered saliva: Fresh whole saliva was collected from a healthy young subject (age 36). Saliva was stimulated by chewing on paraffin wax. The saliva was added to PBS in a 1:1 ratio (v/v), and sterilized by filtration through a 0.20 [micron vacuum driven filtration system (STERICUP™, Millipore Corporation, Bedford, Mass., U.S.A.).

Experimental protocol: To test tubes containing 1 ml of Decarboxylase media 2 ml. whole saliva or filtered saliva (as a negative control) were added. The test tubes were supplemented with 90 mg of various natural products (3% w/v), as indicated. These products included: *Echinacea* (*Echinacea augustifolia*) roots, Mastic gum (*Pestacia lentiscus*) resin, Sage (*Salvia officinalis*) leaves and Lavender (*Lavandula augustifolia*) flowers. These natural products were provided by Agrimed, Weizmann Institute (Ness-Ziona, Israel) as dried material and were ground using a pestle and mortar. Test tubes were incubated at 37 degrees Celsius for 72 hours under anaerobic conditions. Anaerobic conditions were obtained by using an anaerobic jar and ANAEROGEN TM anaerobic kit (Oxoid, Hampshire, UK). Following incubation, salivary protein degradation and malodor related parameters were determined. The experiment was done in six replicates.

Volatile sulfide compounds (VSC): Volatile sulfide levels were measured in the test tubes using a HALIMETER™ sulfide monitor (InterScan Corp., Chatsworth, Calif., USA). The monitor was zeroed on ambient air, and a one quarter inch diameter disposable plastic straw was attached to the air inlet of the monitor. Test tubes headspace VSC levels were measured by inserting the other end of the straw 2 cm into each test tube immediately after removing the cap, and recording the maximal reading in ppb sulfide equivalents.

Organoleptic measurements: Malodor production levels were scored by an experienced odor tester blinded to the contents of each test tube. Test tubes were randomized and the measurement of malodor levels was performed by sniffing the malodor emanating from each test tube, immediately after shaking and opening the test tubes. judge scores were recorded using a scale of 0 to 5, with description as follows: 0, no appreciable odor; 1, barely noticeable odor; 2, slight, but clearly noticeable odor; 3, moderate odor; 4, strong odor; 5, extremely foul odor. Scores between integers (e.g., 2.5) were permitted.

Salivary protein analysis by SDS-PAGE densitometry: Each test tube was sampled for protein analysis. Samples (40 microL) were prepared according to Laemmli (Laemmli UK. Cleavage of structural proteins during the assembly of the head of bacteriophage T4. Nature 1970; 227: 680-685). Samples were boiled for 2 min in sample buffer containing: glycerol, SDS, separating gel buffer and bromophenol blue, and applied to a 12% polyacrylamide gel in Tris-glycine-SDS buffer (0.025 M Tris, 0.192 M glycine, 0.1% SDS, pH 8.6) followed by electrophoresis (80 V) using Mini-PROTEAN 3 electrophoresis minigel cell system, (Bio Rad, Hercules, Calif., USA). Gels were stained with Coomassie brilliant blue (Bio Rad, Hercules, Calif., USA). Salivary protein levels were determined densitometrically (B.I.S. 202 D Bio imaging system, Jerusalem, Israel) by comparing intensities of the stained bands to the filtered saliva control.

Bacterial measurements: Viable counts were performed by plating of 10 (microL) aliquots in serial ten-fold dilutions in PBS onto Brain-Heart infusion agar plates (Hy-Labs, Rehovot, Israel). Plates were incubated at 37 degrees Celsius for 24 h under both aerobic and anaerobic conditions. Predominant microbial forms were evaluated microscopically following Gram staining (Sigma) of incubation mixture samples (10 microL).

In Vivo Study

Fabrication of tablets: Hydroxypropylcellulose (HPC; 34 mg) and Carpool (CP; 136 mg) were mixed with chlorhexidine (CHX), zinc gluconate or natural medicinals formulation: (*Echinacea* (*Echinacea augustifolia*) root, Mastic gum (*Pestada lentiscus*) resin, Lavender (*lavandula augustifolia*) flowers and Sage (*salvia officinals*) leaves) (30 mg) using mortar and pestle. Tablets of 12 mm diameter, with one flat surface facing the oral cavity, and one convex side, pointing to the palate with maximum thickness of 2.5 mm, and 200 mg by weight, were pressed using laboratory Carver press (Carver Machine Works, Inc, In, USA), with a pressure of 5 ton/cm2 for 30 seconds. Plain tablets of the same size and weight (200 mg) were prepared by compression molding of the bioadhesive polymers without the active ingredients.

Study population: A total of 35 young healthy volunteers, aged between 20 and 30 years old, were included in the study. Volunteers were asked to refrain from any type of oral activity: eating, drinking, brushing, oral rinsing, and chewing gum for at least two hours prior to the experiment. They were also instructed not to brush their teeth, floss or use commercial mouth rinses or other breath fresheners on the day of the examination. Experimental protocol was approved by Helsinki committee, registered in clinical registration system NCT00250289 and an informed consent was obtained.

Experimental protocol: Malodor related parameters baseline measurements were conducted at the beginning of the experiment. Measurements included organoleptic measurements (odor judge scores) and volatile sulfide levels measurements using a sulfide monitor (HALIMETER™). Following baseline measurements the volunteers were randomly assigned to one of four treatment groups; palatal patch containing natural medicinals formulation, zinc, chlorhexidine or no active ingredient (placebo). Measurements of malodor related parameters were conducted every 5 minutes during the first hour and every 15 minutes during the second hour of the experiment.

Volatile sulfide compounds (VSC): Volatile sulfide levels were measured using a sulfide monitor (HALIMETER™, InterScan Crop., Chatsworth, Calif., USA). The monitor was zeroed on ambient air before each measurement was taken. A Teflon tube connected to a flexible drinking straw was attached to the air inlet of the monitor. For each measurement, the straw was inserted 5 cm into the partially opened mouth. Readings of peak ppb of sulfide equivalents were recorded.

Organoleptic measurements: The participants were asked to keep their mouths closed and refrain from talking for 60 seconds. After one minute, participants were instructed to breathe out gently at a distance of 10 cm from the nose of the odor judge who recorded the malodor using a scale of 0 to 5, as follows:

0—no appreciable odor.
1—barely noticeable odor.
2—slight, but clearly noticeable odor.
3—moderate odor.
4—strong odor.
5—extremely foul odor.

Statistical analysis: The various products were compared for each parameter using ANOVA test with Dunnett multiple pair-wise comparisons, which compared each medicinal to the whole saliva control. Statistical tests were two tailed and p-value of 0.05 or less was considered statistically significant.

Figure 10:
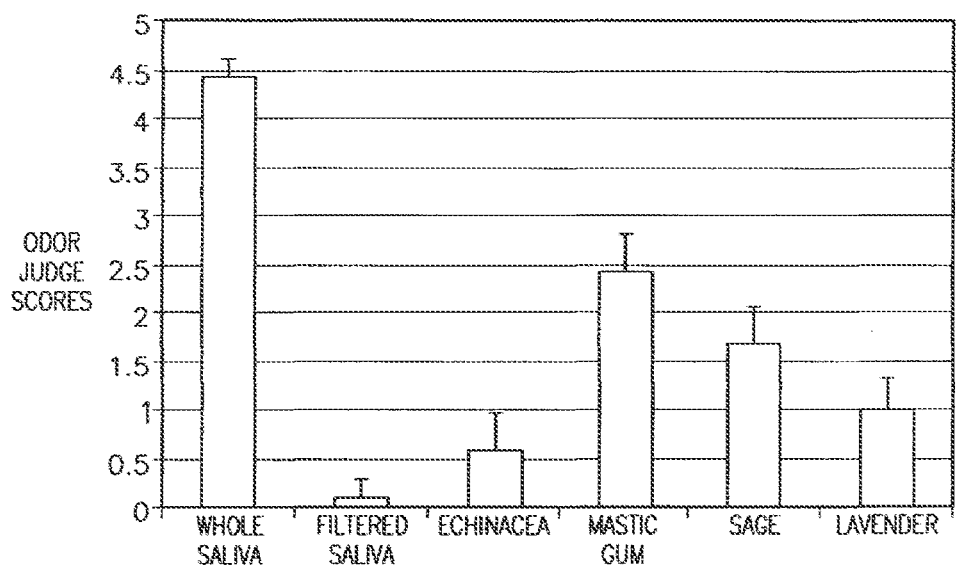
FIG. 10 is a graphical illustration showing odor scores assesed by a professional odor tester for malodor production for herbs tested and for controls.

Results—In Vitro Study:

Reference is now made to FIG. 10, which is a graphical illustration showing the odor scores of professional tester for malodor production for each of the herbs tested and for controls. Results showed that whereas all of the various products caused some reduction in malodor production from the incubated whole saliva (p<0.001), *Echinacea* and Lavender were the most effective ones, yielding odor judge scores of 0.6 and 1 respectively. *Echinacea* decreased malodor production by 86% and Lavender by 77% as compared to the whole saliva control.

Figure 11:
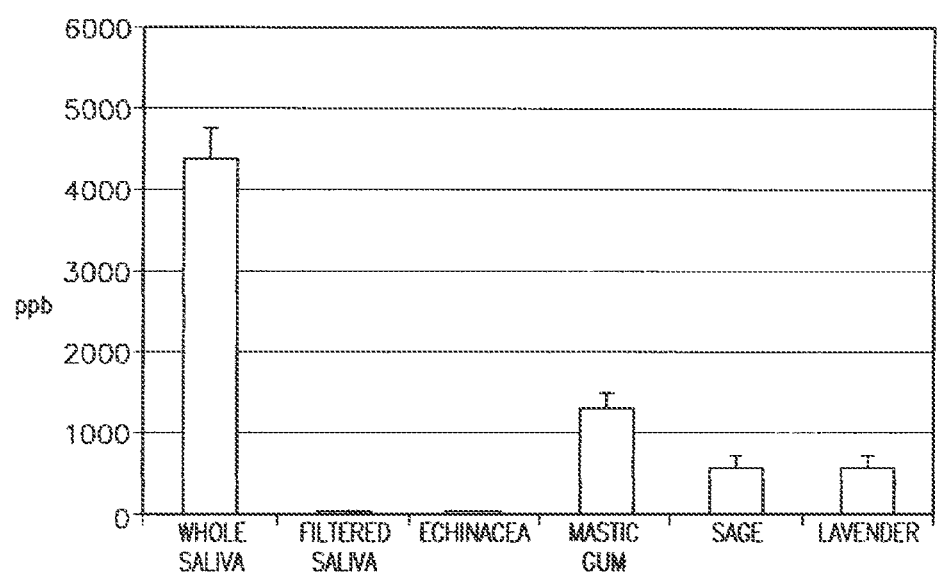
FIG. 11 is a graphical illustration of VSC production for herbs tested and controls.

Reference is now made to FIG. 11, which is a graphical illustration of VSC production (in ppb). *Echinacea* and Lavender show a marked reduction in VSC headspace levels of the incubated saliva.

Figure 12:
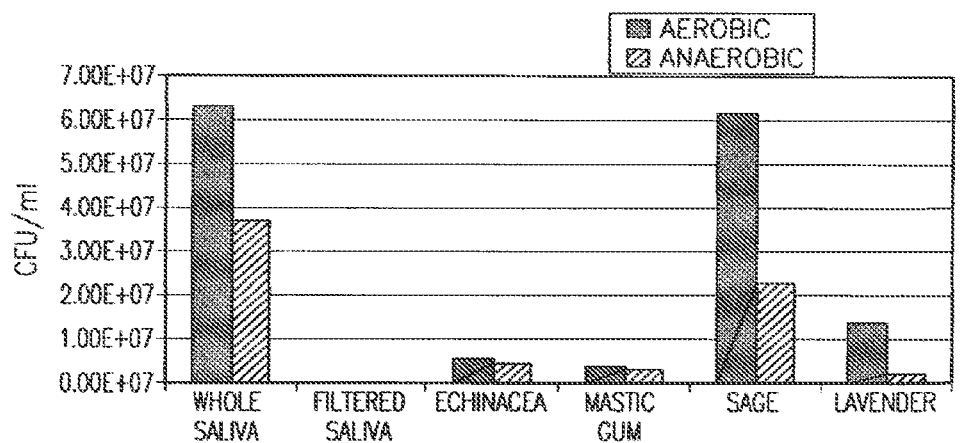
FIG. 12 is a graphical illustration of antibacterial activity in CFU/ml for each of the herbs tested and for controls.

Reference is now made to FIG. 12, which is a graphical illustration of antibacterial activity in CFU/ml for each of the herbs and controls. Mastic gum and *Echinacea* demonstrated the most pronounced antimicrobial effect, as seen by the reduction in viable counts for both aerobic and anaerobic conditions. Bacterial shift towards a more predominantly Gram-positive bacterial population was caused mainly by *Echinacea* and Lavender. Furthermore, Lavender showed a stronger inhibitory effect on the anaerobic bacterial population as can be seen by the reduction in viable counts for these bacteria.

Figure 13:
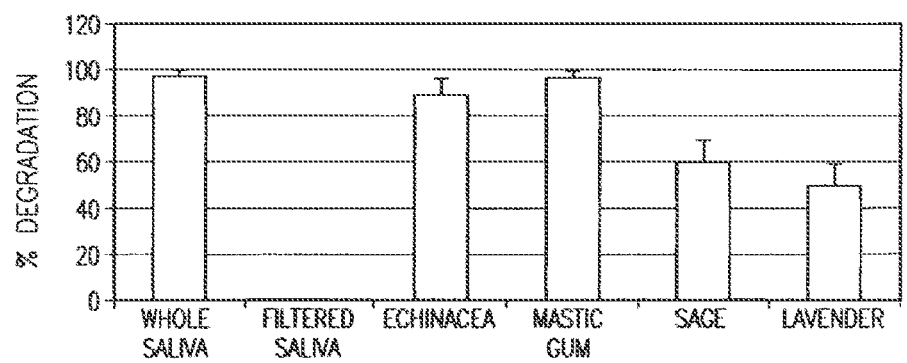
FIG. 13 is a graphical illustration showing salivary protein degradation.

Reference is now made to FIG. 13, which is a graphical illustration showing salivary protein degradation. Salivary protein degradation inhibition was most pronounced in the presence of Sage, Lavender and Thyme. Lavender decreased salivary protein degradation by 48% as compared to the whole saliva control.

Interestingly, the combination of the four natural medicinals resulted in a synergistic effect on malodor and volatile sulfide reduction as can be seen from TABLE 1.

TABLE 1

| | Combined treatment | | |
|---|---|---|---|
| Medicinal Plant | Malodor Production | Volatile Sulfide Compounds (ppb) | pH |
| Echinacea | 0.5 | 60 | 5 |
| Mastic Gum | 2.5 | 2000 | 7.5 |
| Sage | 1.5 | 1600 | 6 |
| Lavender | 1 | 1300 | 6 |
| Echinacea + Lavender | 0 | 560 | 5 |
| Echinacea + Mastic Gum + Sage + Lavender | 0 | 45 | 5.5 |
| Control (filtered saliva) | 0 | 51 | 6 |
| Control (whole saliva) | 4.5 | 40000 | 6 |

In Vivo Study

Figure 14:
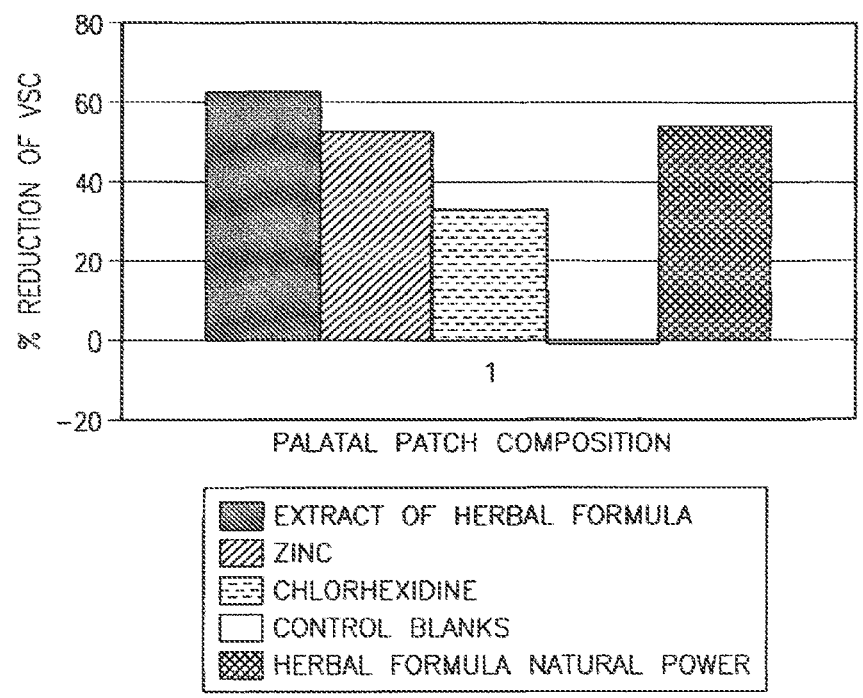
FIG. 14 is a graphical illustration showing comparative reduction of VSC using various compositions of a palatal patch, in accordance with embodiments of the present invention.
Figure 15:
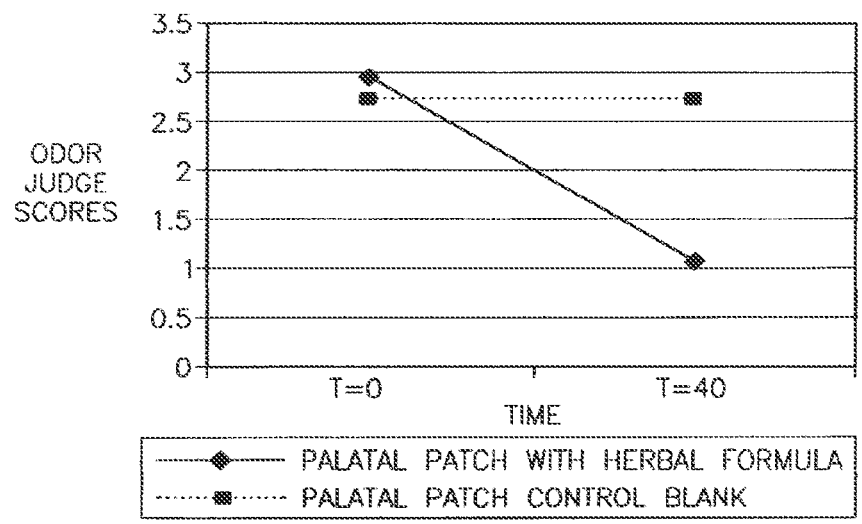
FIG. 15 is a graphical illustration showing professional tester odor scores for malodor production for each of the herbs tested and for controls in an in-vivo study.

Reference is now made to FIG. 14, which is a graphical illustration showing comparative reduction of VSC using various compositions of palatal patch. The palatal patch comprising the natural medicinal formulation was the most effective treatment. This treatment resulted in a 60% reduction in volatile sulfide levels, and was twice as effective Reference is now made to FIG. 15, which is a graphical illustration showing the odor scores of professional tester for malodor production for each of the herbs tested and for controls. Malodor reduction was significant for the palatal patch with herbal composition, resulting in a reduction in odor judge scores from score 3 to score 1 (barely noticeable odor), as compared to the placebo.

Discussion

Results of the present study demonstrate the synergistic and non-synergistic anti-malodorous activity of a formulation comprised of four natural medicinals. These include: *Echinacea* (*Echinacea augustifolia*) root, Mastic gum (*Pestada lentiscus*) resin, Lavender (*Lavandula augustifolia*) flowers and Sage (*Salvia officinalis*) leaves. The formulation proved active both in vitro in a salivary incubation assay and in vivo, in a clinical study.

Using the different parameters measured in the in vitro study, the potency and mechanism of action through which each substance affects malodor production was determined. Furthermore, this study demonstrated that the combination of these four herbs caused a synergistic effect resulting in a greater reduction in malodor then each substance individually.

The in vivo study in which the combination of the four herbs served as the active ingredient of a palatal patch proved the clinical effectiveness of this formulation as a valid treatment for oral malodor. Furthermore, in this study the effect of the natural herbal formulation on volatile sulfide reduction was greater than that of two known active anti-malodorous agents: chlorhexidine and zinc.

Malodor might be inhibited at several points along its production process: (i) substrate availability—inhibition of proteolytic activity will reduce the formation of malodorous by-products, (ii) bacterial population—reduction in bacterial load, especially Gram negative microorganisms and a floral shift towards a more Gram positive population will cause reduction in malodor production, (iii) volatility—even once the volatile malodorous compounds have been produced they could still be converted into nonvolatile compounds (e.g. VSC conversion) by means of chemical bonds, oxidation or pH reduction thus rendering them unnoticeable.

For instance, antimicrobial activity, especially against the Gram-negative microorganisms, might explain the anti-malodorous activity of Lavender. Inhibition of proteolytic degradation of salivary proteins might explain the effect of Sage and Thyme on malodor production. Finally, pH reduction and VSC conversion to non-volatile compounds might explain the effectiveness of Echinacea in malodor and VSC reduction despite its inability to inhibit salivary protein degradation. The pH might be altered directly by the chemical traits of the substance added or indirectly by affecting the microbial population. Gram positive oral bacteria (mainly streptococci) tend to use sugar fermentation for energy production, a process that results in acid production and pH reduction. On the other hand, Gram negative oral bacteria relay mainly on protein degradation and amino acid utilization which propagates pH elevation. The understanding of the mechanism of action for each material tested and its efficacy also helped in suggesting the combinations of the four medicinals in order to gain a synergistic effect from their combined action. Suggested mechanisms were based on the in-vitro study, and were hypothesized to include sulfide binding for Echinacea, proteolysis inhibition for sage and lavender, and antimicrobial action for mastic gum.

Example 2

Materials: Hydroxypropyl (HPC), cellulose—with average molecular weight of 1,150,000 Da was obtained from Hercules Co. Ltd. (klucel HF, Wilmington, Del.), Carpool (CP), was obtained from Goodrish Co. Ltd. (Cleveland, Ohio). Medicinals included: Echinacea (Echinacea augustifblia) root, Mastic gum (Pestacia lentiscus) resin, Lavender (lavandula augustifolia) flowers and Sage (salvia officinalis) leaves and were provided by herbal farm Herbalife Co. Ltd. (Lod IL) as dried powder.

Methods: A total of 67 volunteers, were divided into five groups:
1. HF—palatal patch consisting the herbal formula as natural powder (N=14)
2. HE—palatal patch consisting an extract of the herbal formula (N=9).
3. CH—palatal patch consisting chlorhexidine gluconate (N=8). [
4. Z—palatal patch consisting zinc (N=11). [0106]
5. C—palatal patch consisting the adhesive polymers menthol and sorbitol as control blanks (N=26).

The mixtures were pressed as an oval tablet. Fabrication of tablets was as following. Dry powder of herbal medicinal was mixed in a ratio of 1:1:1:1. HPC (34 mg) and CP (136 mg) were mixed with the herbal mixture (30 mg) using mortar and pestle. Tablets of 12 mm diameter, with one flat surface facing the oral cavity, and one convex side, pointing to the palate with maximum thickness of 2.5 mm, and 200 mg by weight, were pressed using laboratory Carver press (Carver Machine Works, Inc, In, USA), with a pressure of 5 ton/cm2 for 30 seconds. As for the control, plain tablets of the same size and weight (200 mg) were prepared by compression molding of the polymers powder without actives.

Manufacture of Tablet

For 10 tablets: HPC (400 mg) and CP (1600 mg) were mixed with the medicinals (1000 mg) using mortar and pestle. Tablets of 12-mm diameter, 2-mm thick, weighing 300 mg were pressed by laboratory carver press (Carver Machine Works, Inc., Washington, N.C.) using a pressure of 3 ton/cm2 for 20 sec.

Tablets were attached to the hard palate of the subjects. Oral malodor levels were scored by two odor judges, Volatile sulfide levels (VSC) were measured using a sulfide monitor (Halimeter™). Measurements were taken before and during treatment. Measurements of the volatile sulfide levels and Organolrptic measurements were done every 5 minutes in the first hour and every 15 minutes in the second hour.

Results: Oral malodor reduced significantly ($p<0.05$) following palatal patch application. Maximal reduction was reached after 20 minutes malodor levels remained low for the entire duration of the experiment (120 min).

Figure 16:
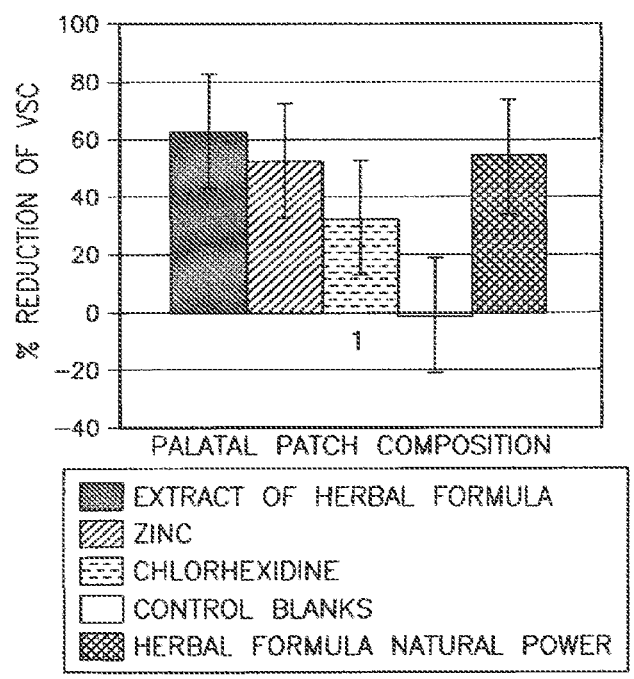
FIG. 16 is a graphical illustration of the comparative reduction of VSC levels for different patch compositions.

Reference is now made to FIG. 16, which is a graphical illustration of the comparative reduction of VSC levels for the different patch compositions. The control (C) is inactive and proves that the polymeric and taste ingredients are not active in reducing the odor score, whereas the active ingredients: HE, HF, Z and CH actively reduced odor scores. HE slightly better than HF and Z and much better than CH.

Figure 17:
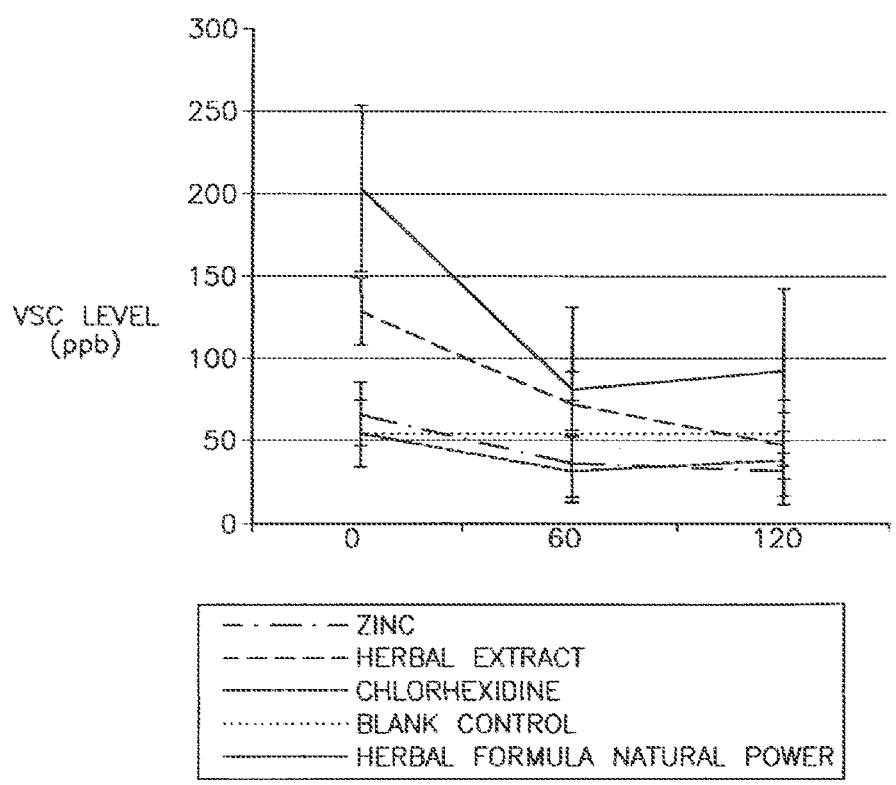
FIG. 17 is a graphical illustration of VSC levels overtime.

Reference is now made to FIG. 17, which is a graphical illustration of VSC levels over time. The results of FIG. 17 demonstrate that the HE patches remained active for the entire 120 minutes of the test whereas HF, CH and Z remained active for only 60 minutes, after which the odor scores elevated again.

All the volunteers except for one carried the palatal patch for two hours and did not report any discomfort. The volunteer that asked it to be removed after 1 hour reported gag reflex as cause for terminating the test, retentiveness of the patch was satisfactory and maintained it in situ for the whole duration of the test. Zinc group reported dry sensation of the mouth. The chosen position of the patch was proven to be relatively convenient and the compliance to the herbal and polymeric ingredients was good.

It should be noted that lyophilized herbal formula seem to be more effective than herbs as natural powder. In addition, propolis, thyme and chamomile can enhance the antibacterial effect of the formula.

Example 3

The aim of this experiment was to test the combined effect of the herbal active ingredients; Mastic gum, Sage, Lavender and Echinacea on volatile sulfide compounds (VSC) production in a salivary incubation assay.

Experiment Protocol

Salivary incubation assay—1 mL fresh whole saliva was incubated in 2 mL Decarboxylase media with 0.5%, 1%, 2% and 3% (w/v) of the tested herbs. Incubation mixtures were incubated under anaerobic conditions at 37° C. for 72 hours (Sterer and Rubinstein 2005). Following incubation, headspace VSC levels in the test tubes were determined using a sulfide monitor. Experiment was done in six replicates and the results were presented in a diagram and analyzed using two tailed analysis of variance (ANOVA).

Specifically the following combinations of herbal composition were tested:
1—MASTIC GUM;
2—MASTIC GUM+SAGE;
3—MASTIC GUM+SAGE+LAVENDER;
4—MASTIC GUM+SAGE+LAVENDER+ECHINACEA.

Results and Conclusions

Figure 18:
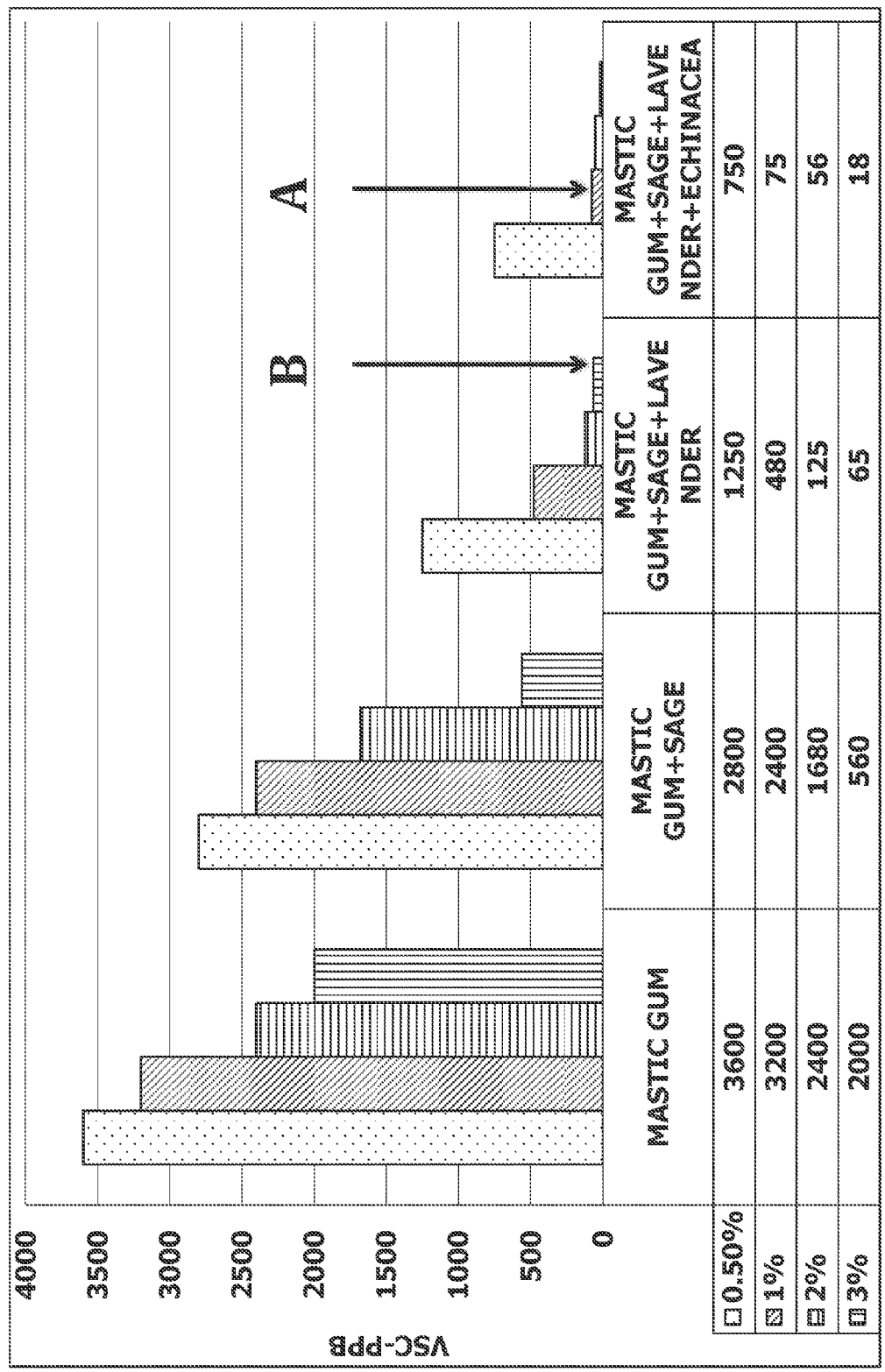
FIG. 18 is a bar chart attesting a synergistic effect indicated by arrow A, showing an effective reduction of volatile sulfide compounds (VSC) to concentrations of 75 part per billion (PPB) achieved by combining *Echinacea*, Lavender, Mastic Gum and Sage, in amounts essentially not exceeding 1% (w/v) of the weight of each compound per volume of the saliva.

Reference is now made to FIG. 18, showing a bar chart comparing the effect on the concentration of volatile sulfide compounds (VSC) in part per billion (PPB) achieved by various combinations of herbal composition, in concentrations of 0.5%, 1%, 2% and 3% (w/v) of the weight of each herbal compound per volume of the saliva.

The surprising discovery of this study is that the combination of all four compounds (namely: *Echinacea*, Lavender, Mastic Gum and Sage), in amounts not exceeding 1% of each compound weight relatively to the volume of the saliva, possesses a synergistic effect achieving reduction of volatile sulfide compounds (VSC) to concentrations of 75 part per billion (PPB). The bar indicated by arrow A on the bar chart of FIG. 18 shows that an effective reduction of volatile sulfide compounds (VSC) to concentrations of 75 part per billion (PPB) was achieved by combining all four compounds, in amounts essentially not exceeding 1% (w/v) of the weight of each compound relatively to the volume of the saliva.

The aforementioned synergistic effect, reflected in the bar chart of FIG. 18 indicated by arrow A, entails several utilitarian benefits. Some of the ingredients and particularly Mastic Gum are expensive. Therefore reducing the amounts of such expensive ingredients provides for a more affordable medicine for treatment of halitosis. Such more affordable medicine for treatment of halitosis is especially desirable in view of the fact that the claimed composition is not to be used merely once or few times but rather to be constantly applied on a daily basis. Furthermore, some of the ingredients, particularly *Echinacea* and Sage, may have an undesirable sensory and/or flavor qualities. Therefore reducing the amounts of such ingredients provides for a composition that is more optimal for human consumption.

Moreover the discovery that all four compounds (namely: *Echinacea*, Lavender, Mastic Gum and Sage) possess a synergistic effect and achieve reduction of volatile sulfide compounds (VSC) in amounts not exceeding 1% each is pivotal for creating a medicine for treatment of halitosis which has much longer lasting effect. It should be appreciated that the synergic composition is applied to the secreted saliva, wherein the concentration of the active ingredients is constantly reduced, typically in a form of a decay curve, due to a gradual melting away of the excipient and overall mass/size reduction of the composition. The discovery that all four ingredients, in amounts essentially not exceeding 1% each, achieve the desired reduction of VSC, allows achieving a desired reduction of VSC for a much longer time, by using excipient having slower dissolution rates.

Here is the place to mention that a similar effect can be achieved without the unexpected synergistic effect of combining all four compounds, however, in much higher concentrations. For instance using only Lavender, Mastic Gum and Sage achieving reduction of volatile sulfide compounds (VSC) to concentration of 65 (PPB), however, in amounts about 3% each of compound weight relatively to the volume of the saliva, as shown by the bar indicated with arrow B.

What is claimed is:

1. A method of manufacturing a medicine for treatment of halitosis, said medicine being applicable to saliva secreted into oral cavity, said method comprises:
   (a) determining a target salivation rate at which said saliva secreted into said oral cavity;
   (b) selecting a desired effective duration time for a single serving dosage of said medicine, wherein during said desired effective duration of time a concentration of said medicine in said saliva within said oral cavity is sufficient to effectively prevent halitosis;
   (c) calculating or defining a diffusion coefficient of an appropriate pharmaceutical excipient configured to dissolve at a predefined dissolution rate within said saliva;
   (d) respectively defining or calculating a total mass of said pharmaceutical excipient to be used for said single serving dosage of said medicine;
   (e) calculating a total mass of an active ingredient to be used for said single serving dosage of said medicine in combination with said pharmaceutical excipient, wherein said active ingredient comprises a herbal composition comprising:
      (1) an effective amount of *Echinacea* configured to sustain a concentration which does not exceed one percent of weight of said *Echinacea* per volume of said saliva, at least during said desired effective duration of time;
      (2) an effective amount of Lavender configured to sustain a concentration which does not exceed one percent of weight of said Lavender per volume of said saliva, at least during said desired effective duration of time;
      (3) an effective amount of Mastic Gum configured to sustain a concentration which does not exceed one percent of weight of said Mastic Gum per volume of said saliva, at least during said desired effective duration of time, and
      (4) an effective amount of Sage configured to sustain a concentration which does not exceed one percent of weight of said Sage per volume of said saliva, at least during said desired effective duration of time;
   (f) formulating said pharmaceutical excipient and said active ingredient into said single serving dosage of said medicine.

2. The method of manufacturing a medicine for treatment of halitosis, as in claim 1, wherein said composition further comprises at least one of: Propolis, Elder, Thyme and Chamomile.

3. The method of manufacturing a medicine for treatment of halitosis, as in claim 1, wherein said composition is formed into a palatal patch.

4. The method of manufacturing a medicine for treatment of halitosis, as in claim 1, wherein said composition is formed into at least one of: a toothpaste, candy and chewing gum.

5. The method of manufacturing a medicine for treatment of halitosis, as in claim 1, wherein a weight ratio of *Echinacea*, Lavender, Sage and Mastic Gum in said composition is 1:1:1:1.

6. The method of manufacturing a medicine for treatment of halitosis, as in claim 1, wherein said step of calculating or defining a diffusion coefficient of an appropriate pharmaceutical excipient configured to dissolve at a predefined dissolution rate within said saliva or said step of respectively defining or calculating a total mass of said pharmaceutical excipient to be used for said single serving dosage of said medicine is performed in accordance with the following Equation 1:

$$\frac{dm}{dt} = A\frac{D}{d}(C_s - C_b) \qquad \text{Equation 1}$$

wherein: m is mass of said excipient; t is said target duration time; A is a surface area between said single serving dosage and said saliva; D is said diffusion coefficient of said excipient, d is thickness of a boundary layer of said saliva at a surface of said excipient, $C_s$ is a mass concentration of said excipient on a surface and $C_b$ is a mass concentration of said excipient.

7. A composition for treatment of halitosis, applicable into oral cavity, said composition comprises:
  (a) a pharmaceutical excipient configured to dissolve at a predefined dissolution rate within saliva secreted into said oral cavity;
  (b) an effective amount of *Echinacea* configured to sustain a concentration which does not exceed one percent of weight of said *Echinacea* per volume of said saliva;
  (c) an effective amount of Lavender, wherein said effective amount of Lavender is configured to sustain a concentration which does not exceed one percent of weight thereof to a volume of said saliva;
  (d) an effective amount of Mastic Gum, wherein said effective amount of Mastic Gum is configured to sustain a concentration which does not exceed one percent of weight thereof to a volume of said saliva, and
  (e) an effective amount of Sage, wherein said effective amount of Mastic Gum is configured to sustain a concentration which does not exceed one percent of weight thereof to a volume of said saliva.

8. The composition of claim 7, further comprises at least one of Propolis, Elder, Thyme and Chamomile.

9. The composition of claim 7, formed into a palatal patch.

10. The composition of claim 7, formed into at least one of: a toothpaste, candy and chewing gum.

11. The composition of claim 7, wherein a weight ratio of *Echinacea*, Lavender, Sage and Mastic Gum is 1:1:1:1.

12. The composition of claim 7, formulated into a single serving dosage of said medicine is performed in accordance with Equation 1:

$$\frac{dm}{dt} = A\frac{D}{d}(C_s - C_b) \quad \text{Equation 1}$$

wherein: m is mass of said excipient; t is a target duration of time; A is a surface area between said single serving dosage and said saliva; D is a diffusion coefficient of said excipient, d is thickness of a boundary layer of said saliva at a surface of said excipient, $C_s$ is a mass concentration of said excipient on a surface and $C_b$, is a mass concentration of said excipient.

13. A method of treating halitosis comprises:
  (a) providing an effective amount of *Echinacea* configured to sustain a concentration which does not exceed one percent of weight of said *Echinacea* per volume of saliva, at least during a desired effective duration of time;
  (b) providing an effective amount of Lavender configured to sustain a concentration which does not exceed one percent of weight of said Lavender per volume of saliva, at least during said desired effective duration of time;
  (c) providing an effective amount of Mastic Gum configured to sustain a concentration which does not exceed one percent of weight of said Mastic Gum per volume of said saliva, at least during said desired effective duration of time, and
  (d) providing an effective amount of Sage configured to sustain a concentration which does not exceed one percent of weight of said Sage per volume of said saliva, at least during said desired effective duration of time.

14. The method of claim 13 further comprises providing at least one of Propolis, Elder, Thyme and Chamomile.

15. The method of claim 13 further comprises forming said ingredients into a palatal patch.

16. The method of claim 13 further comprises forming said ingredients into at least one of: a toothpaste, candy and chewing gum.

17. The method of claim 13 wherein a weight ratio of *Echinacea*, Lavender, Sage and Mastic Gum is 1:1:1:1.

18. The method of claim 13 further comprises formulating said ingredients with a pharmaceutical excipient into a single serving dosage according to Equation 1:

$$\frac{dm}{dt} = A\frac{D}{d}(C_s - C_b) \quad \text{Equation 1}$$

wherein: m is mass of said excipient; t is a target duration of time; A is a surface area between said single serving dosage and said saliva; D is a diffusion coefficient of said excipient, d is thickness of a boundary layer of said saliva. at a surface of said excipient, $C_s$ is a mass concentration of said excipient on a surface and $C_b$ is a mass concentration of said excipient.

* * * * *